(12) United States Patent
Huang et al.

(10) Patent No.: US 12,201,481 B2
(45) Date of Patent: Jan. 21, 2025

(54) METHODS AND SYSTEMS FOR SPECKLE REDUCTION IN ULTRASOUND IMAGES BY COMPOUNDING SUB-IMAGES ASSOCIATED WITH DIFFERENT RECEIVE ANGLES

(71) Applicant: KONINKLIJKE PHILIPS N.V., Eindhoven (NL)

(72) Inventors: Sheng-Wen Huang, Ossining, NY (US); Changhong Hu, Bothell, WA (US); Francois Guy Gerard Marie Vignon, Andover, MA (US); Jun Seob Shin, Winchester, MA (US); Unmin Bae, Kenmore, WA (US); Neil Reid Owen, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 257 days.

(21) Appl. No.: 17/617,374

(22) PCT Filed: Jun. 11, 2020

(86) PCT No.: PCT/EP2020/066153
§ 371 (c)(1),
(2) Date: Dec. 8, 2021

(87) PCT Pub. No.: WO2020/249651
PCT Pub. Date: Dec. 17, 2020

(65) Prior Publication Data
US 2022/0249064 A1     Aug. 11, 2022

Related U.S. Application Data

(60) Provisional application No. 62/859,966, filed on Jun. 11, 2019.

(51) Int. Cl.
*A61B 8/08*     (2006.01)
*A61B 8/00*     (2006.01)
(Continued)

(52) U.S. Cl.
CPC .......... *A61B 8/5269* (2013.01); *A61B 8/4483* (2013.01); *A61B 8/5207* (2013.01);
(Continued)

(58) Field of Classification Search
CPC ............. G01S 15/8995; G01S 15/8927; G01S 7/52095
See application file for complete search history.

(56) References Cited

U.S. PATENT DOCUMENTS 6,443,896 B1    9/2002  Detmer
6,508,770 B1    1/2003  Cai
(Continued)

FOREIGN PATENT DOCUMENTS

WO        2005024462 A1    3/2005
WO    WO-2005059591 A1 *  6/2005   ............... A61B 8/14
WO    WO-2017220354 A1 * 12/2017   ......... G01S 15/8927

OTHER PUBLICATIONS

International Search Report and Written Opinion for PCT/EP2020/066153; Date of Mailing: Sep. 15, 2020, 12 pages.

*Primary Examiner* — Joel Lamprecht
*Assistant Examiner* — Nyrobi Celestine

(57)     ABSTRACT

Systems and methods for reducing speckle while maintaining frame rate are disclosed. Multiple sub-images associated with different receive angles are acquired for a single transmit/receive event at an observation angle. The sub-images are compounded to generate a final image with reduced speckle. In some examples, multiple sub-images from multiple transmit/receive events are compounded to generate the final image. The observation angle and/or the receive angles may vary between transmit/receive events in some examples.

23 Claims, 6 Drawing Sheets

(51) Int. Cl.
*G06T 5/50* (2006.01)
*G06T 5/70* (2024.01)

(52) U.S. Cl.
CPC .............. *A61B 8/54* (2013.01); *G06T 5/50* (2013.01); *G06T 5/70* (2024.01); *A61B 8/5246* (2013.01); *G06T 2207/10132* (2013.01); *G06T 2207/20212* (2013.01); *G06T 2207/30004* (2013.01)

(56) References Cited

U.S. PATENT DOCUMENTS

| | | | |
|---|---|---|---|
| 6,530,885 B1 | 3/2003 | Entrekin et al. | |
| 6,544,177 B1* | 4/2003 | Robinson | G01S 15/8995 600/443 |
| 6,695,783 B2 | 2/2004 | Henderson et al. | |
| 8,137,272 B2 | 3/2012 | Cooley et al. | |
| 2006/0058670 A1* | 3/2006 | Lin | G01S 7/52047 600/447 |
| 2008/0183079 A1 | 7/2008 | Lundberg | |
| 2008/0242992 A1* | 10/2008 | Criton | G01S 15/8995 600/447 |
| 2011/0046486 A1 | 2/2011 | Shin et al. | |
| 2011/0306886 A1* | 12/2011 | Daft | G01S 15/8915 600/459 |
| 2012/0157850 A1* | 6/2012 | Sumi | A61B 8/145 600/443 |
| 2012/0203105 A1* | 8/2012 | Yamamoto | A61B 8/56 600/443 |
| 2013/0258805 A1* | 10/2013 | Hansen | G01S 7/52046 367/8 |
| 2014/0046187 A1* | 2/2014 | Taniguchi | A61B 8/463 600/444 |
| 2015/0011882 A1 | 1/2015 | Abe | |
| 2016/0282467 A1* | 9/2016 | Olsson | G01S 15/8925 |
| 2020/0008784 A1* | 1/2020 | Yamanaka | G01S 7/52038 |

\* cited by examiner

METHODS AND SYSTEMS FOR SPECKLE REDUCTION IN ULTRASOUND IMAGES BY COMPOUNDING SUB-IMAGES ASSOCIATED WITH DIFFERENT RECEIVE ANGLES

CROSS-REFERENCE TO PRIOR APPLICATIONS

This application is the U.S. National Phase application under 35 U.S.C. § 371 of International Application No. PCT/EP2020/066153, filed on Jun. 11, 2020, which claims the benefit of U.S. Provisional Patent Application No. 62/859,966, filed on Jun. 11, 2019. These applications are hereby incorporated by reference herein.

TECHNICAL FIELD

This application relates to speckle reduction. More specifically, this application relates to speckle reduction in ultrasound without reducing frame rates.

BACKGROUND

During an ultrasound exam, when scanning soft tissue, speckle is commonly observed even in a macroscopically uniform region due to random distribution of sub-resolution scatterers. Often speckle is considered as noise, and techniques, such as spatial compounding and frequency compounding, have been developed for reducing its variance. In addition to speckle reduction, spatial compounding often provides better border delineation. However, spatial compounding typically requires multiple transmit/receive events to acquire a frame. This reduces the frame rate of the ultrasound scan, which may be undesirable when observing tissue in motion (e.g., due to hand motion or heartbeat).

SUMMARY

Methods and systems for reducing speckle without reducing frame rate are described. A transducer array may transmit ultrasound beams at an observation angle for a transmit/receive event and receive echo signals resulting from the transmit/receive event. A beamformer may receive signals from transducer elements via channels. The beamformer may selectively delay and sum appropriate signals from the channels to generate sub-images from different receive angles at the same time. The sub-images may be combined to form an image with reduced speckle.

In accordance with at least one example described herein, a medical imaging system may include a transducer array, wherein the transducer array is configured to transmit an ultrasound beam, receive echoes responsive to the ultrasound beam, and generate electrical signals corresponding to the echoes, a controller circuit, wherein the controller circuit is configured to cause the transducer array to transmit the ultrasound beam at an observation angle for a transmit/receive event, and a beamformer, wherein the beamformer is configured to receive the electrical signals from the transmit/receive event and generate a first plurality of beamformed signals, wherein each of the first plurality of beamformed signals is associated with a corresponding one of a first plurality of receive angles, wherein the medical imaging system is configured to compound the first plurality of beamformed signals to generate a final image.

In accordance with at least one example described herein, a method may include transmitting a first ultrasound beam at a first observation angle during a first transmit/receive event, receiving a first plurality of echoes generated responsive to the first transmit/receive event, converting the first plurality of echoes to a corresponding first plurality of electrical signals, generating a first plurality of beamformed signals from the first plurality of electrical signals, wherein individual ones of the first plurality of beamformed signals are associated with corresponding ones of a first plurality of receive angles, compounding the first plurality of beamformed signals to generate a first combined signal, and generating a final image from the first combined signal.

DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Figure 1:
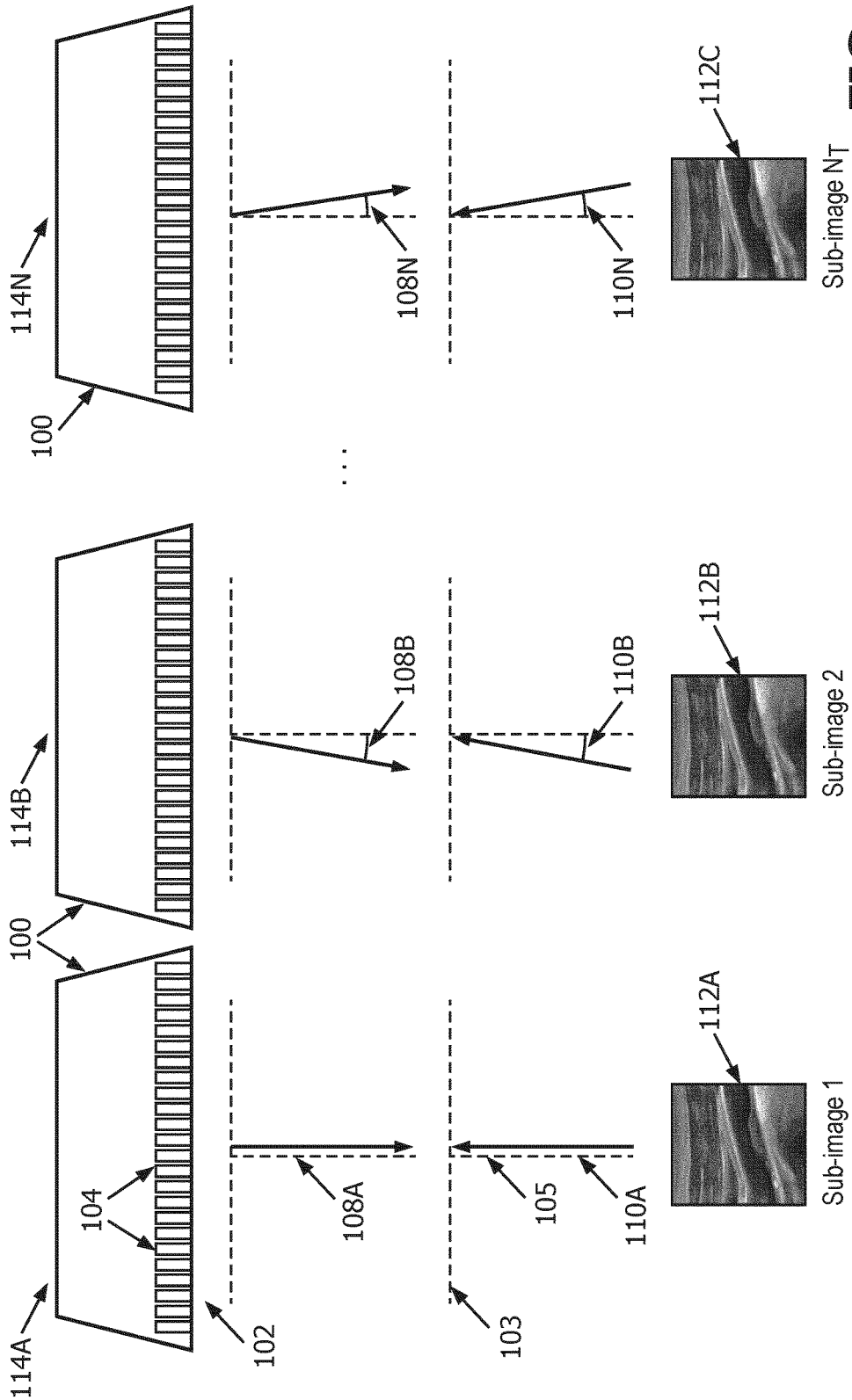
FIG. 1 is an illustration of an example of spatial compounding

FIG. 1 is an illustration of an example of spatial compounding. An ultrasound probe 100 at different points in time i.e. transmit/receive events 114A-N). Ultrasound probe 100 may include a transducer array 102 that includes a plurality of transducer elements 104. The transducer elements 104 may transmit ultrasound beams steered along an observation angle 108A-N and receive corresponding echoes along a receive angle 110A-N for each transmit/receive event 114A-N. The observation angles 110A-N and receive angles 110A-N are shown relative to a plane 105. Plane 105 is normal to a plane 103; plane 103 parallel to the face of the transducer array 102. The observation angle may sometimes be referred to as a transmit steering angle or transmit angle. The received echoes may be used to generate a sub-image 112a-n for each transmit/receive event 114A-N. For spatial compounding, the single ultrasound probe 100 may perform a plurality of transmit/receive events 114A-N, each one at a different observation angle 108A-N and acquire corresponding echoes along different receive angles 110A-N. Spatial compounding may incoherently sum $N_T$ (e.g., three, five, six, nine) sub-images 112A-N to form a final image with reduced speckle (not shown) where $N_T$ is equal to the number of transmit/receive events. In other words, the number of sub-images combined to form the final image is equal to the number of transmit/receive events Spatial compounding may also include averaging the summed images to arrive at a final image. As shown in FIG. 1, in each sub-image 112A-N, the steering angle 110 on receive is tied to the steering angle 108 on transmit. By acquiring images of the same region in $N_T$ directions and then averaging, speckle variation in the final compounded image is reduced, at the cost of lowered effective frame rate by a factor of $N_T$. This frame rate reduction may be undesirable in certain applications, such as those where motion is present.

Example systems and methods that may reduce speckle without reducing frame rate are disclosed herein. As described herein, in some examples, a medical imaging system may include a transducer array configured to transmit an ultrasound beam and receive echoes responsive to the ultrasound beam and generate electrical signals corresponding to the echoes, a controller circuit configured to cause the transducer array to transmit the ultrasound beam at an observation angle, a beamformer configured to receive the electrical signals and generate a plurality of beamformed signals, each of the plurality of beamformed signals associated with a corresponding plurality of receive angles, and a signal processor configured to compound the plurality of beamformed signals to generate a final image. This is in contrast to the system and methods shown in FIG. 1 where beamformed signals associated with only a single receive angle are generated.

As further described herein, in some examples, a medical imaging system may include a transducer array configured to transmit an ultrasound beam and receive echoes responsive to the ultrasound beam and generate electrical signals corresponding to the echoes, a controller circuit configured to cause the transducer array to transmit the ultrasound beam at a first observation angle, and a beamformer configured to receive the electrical signals associated with the first observation angle and generate a plurality of beamformed signals, the plurality of beamformed signals associated with a corresponding plurality of receive angles, wherein the beamformer is further configured to combine the plurality of beamformed signals into a combined signal.

The medical imaging systems described herein may allow speckle reduction without reducing a frame rate of the medical imaging system.

Figure 2:
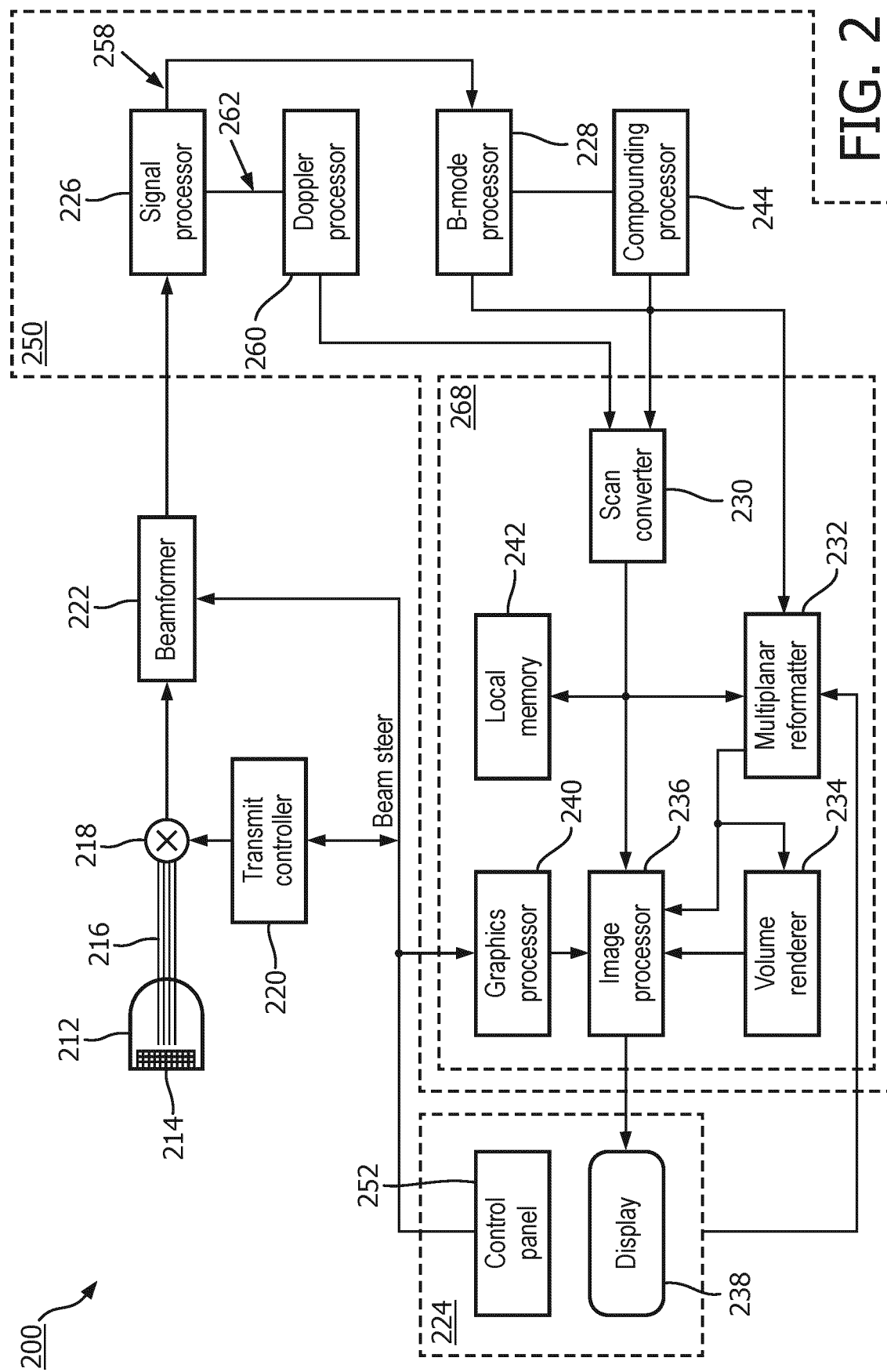
FIG. 2 is a block diagram of an ultrasound imaging system arranged in accordance with some embodiments of the present disclosure.

FIG. 2 shows a block diagram of an ultrasound imaging system 200 constructed in accordance with the principles of the present disclosure. An ultrasound imaging system 200 according to the present disclosure may include a transducer array 214, which may be included in an ultrasound probe 212, for example an external probe or an internal probe such as an intravascular ultrasound (IVUS) catheter probe. In other embodiments, the transducer array 214 may be in the form of a flexible array configured to be conformally applied to a surface of subject to be imaged (e.g., a human patient or an animal). The transducer array 214 is configured to transmit ultrasound signals (e.g., beams, waves) and receive echoes responsive to the ultrasound signals. The transducer elements of the transducer array 214 may convert the echoes from a transmit/receive event into corresponding electrical signals. A variety of transducer arrays may be used, e.g., linear arrays, curved arrays, or phased arrays. The transducer array 214, for example, may include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction In some embodiments, the array 214 may be coupled to a transmit/receive (T/R) switch 218, which switches between transmission and reception and protects the main beamformer 222 from high energy transmit signals. In some embodiments, for example in portable ultrasound systems, the T/R switch 218 and other elements in the system can be included in the ultrasound probe 212 rather than in the ultrasound system base, which may house the image processing electronics. An ultrasound system base typically includes software and hardware components including circuitry for signal processing and image data generation as well as executable instructions for providing a user interface. In some examples, the ultrasound probe 212 may be coupled via a probe cable to the ultrasound system base. In other examples, the ultrasound probe 212 may be wirelessly coupled to the ultrasound system base.

The transmission of ultrasonic signals (e.g., transmit/receive events) from the transducer array 214 is directed by a transmit controller 220, which may be coupled to the T/R switch 218 and a main beamformer 222. In some embodiments, the transmit controller 220 may control the transmission of signals by the transducer elements in the array 214. The transmit controller 220 may control the direction in which beams are steered (e.g., the observation angle). Beams may be steered straight ahead from (orthogonal to) the transducer array 214, or at different angles for a wider field of view. The transmit controller 220 may also be coupled to a user interface 224 and receive input from the user's operation of a user control. In some embodiments, the transmit controller 220 may include a controller circuit (e.g., application specific integrated circuit).

The user interface 224 may include one or more input devices such as a control panel 252, which may include one or more mechanical controls (e.g., buttons, encoders, etc.), touch sensitive controls (e.g., a trackpad, a touchscreen, or the like), and/or other known input devices. The user interface 224 may also include a display 238.

In some embodiments, the electrical signals generated by the transducer elements of the array 214 may be provided via channels 216 to a main beamformer 222 via switch 218 where the electrical signals from individual channels may be combined into a beamformed signal. The beamformer 222 may apply delays to the electrical signals provided on the channels 216 and sum the delayed electrical signals to form the beamformed signal. As described in more detail below, the beamformed signal may be used to generate an image, for example, a B-mode image. The beamformer 222 may be a multiline beamformer. However, instead of the multilines being used to increase the line density of a scanned plane or volume, the multilines may be used to simultaneously acquire multiple sub-images. Examples of multiline beamformers may be found in U.S. Pat. Nos. 6,695,783 and 8,137,272 which are incorporated by reference herein, however, other multiline beamformers may be used.

According to some of the principles of the present disclosure, the beamformer 222 may apply appropriate delays and/or weights to the electrical signals of the channels 216 and/or a subset of the electrical signals and sum the delayed electrical signals to generate a beamformed signal for generating a sub-image associated with a receive angle. Using multiline beamforming capabilities, the beamformer 222 may apply appropriate delays and weights to the electrical signals of the channels 216 from a single transmit/receive event to generate multiple beamformed signals for corresponding sub-images, where each individual sub-image is associated with different receive angles. In some applications, the number of beamformed signals may be limited to a number of multilines of the beamformer 222.

In some embodiments, a microbeamformer (not shown) may be included in probe 212 which may receive the electrical signals from the transducer elements and combine the signals from groups of transducer elements (e.g., patches) and provide the partially beamformed signals to the beamformer 222. Including the microbeamformer may reduce a number of channels required to be provided between the ultrasound probe 212 and the beamformer 222.

In embodiments with and without the microbeamformer, the beamformed signals of beamformer 222 are coupled to processing circuitry 250, which may include one or more processors (e.g., a signal processor 226, a B-mode processor 228, a Doppler processor 260, and one or more image generation and processing components 268) configured to produce an ultrasound image from the beamformed signals (i.e., beamformed RF data).

Processing components 268 may include a scan converter 230, a local memory 242, a graphics processor 240, an image processor 236, a volume renderer 234 and multiplaner reformatter 232.

The signal processor 226 may be configured to process the received beamformed RF data in various ways, such as bandpass filtering, decimation, I and Q component separation, and harmonic signal separation. The signal processor 226 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system 200 may include a B-mode signal path 258 which couples the signals from the signal processor 226 to a B-mode processor 228 for producing B-mode image data.

The B-mode processor may employ amplitude detection for the imaging of structures in the body. The signals produced by the B-mode processor 228 may be coupled to a scan converter 230, a multiplanar reformatter 232, and/or a compounding processor 244. The scan converter 230 may be configured to arrange the echo signals from the spatial relationship in which they were received to a desired image format. For instance, the scan converter 230 may arrange the echo signal into a two dimensional (2D) sector-shaped format, or a pyramidal or otherwise shaped three dimensional (3D) format. The multiplanar reformatter 232 may convert echoes which are received from points in a common plane in a volumetric region of the body into an ultrasonic image (e.g., a B-mode image) of that plane, for example as described in U.S. Pat. No. 6,443,896 (Detmer) incorporated herein by reference. The scan converter 230 and multiplanar reformatter 232 may be implemented as one or more processors in some embodiments.

In some embodiments, the compounding processor 244 may compound the signals associated with the different sub-images to generate a final image and/or a combined signal that may be used to generate a final image. Compounding the signals may include summing the signals processed by the B-mode processor 228 and then taking an average of the summed signal in some examples. In some examples, the total sum may be used to generate the final image. Other compounding techniques may also be used such as taking the maximum value from the sub-images for each pixel. Compounding may be performed on envelope data or log-compressed envelope data. The combined signal or final image may be provided to the B-mode processor 228, the scan converter 230 and/or multiplanar reformatter 232.

A volume renderer 234 may generate an image (also referred to as a projection, render, or rendering) of the 3D dataset as viewed from a given reference point, e.g., as described in U.S. Pat. No. 6,530,885 (Entrekin et al.) incorporated herein by reference. The volume renderer 234 may be implemented as one or more processors in some embodiments. The volume renderer 234 may generate a render, such as a positive render or a negative render, by any known or future known technique such as surface rendering and maximum intensity rendering.

In some embodiments, the system may include a Doppler signal path 262 which couples the output from the signal processor 226 to a Doppler processor 260. The Doppler processor 260 may be configured to estimate the Doppler shift and generate Doppler image data. The Doppler image data may include color data which is then overlaid with B-mode (i.e. grayscale) image data for display. The Doppler processor 260 may be configured to filter out unwanted signals (i.e., noise or clutter associated with non-moving tissue), for example using a wall filter. The Doppler processor 260 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion may also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives may be used instead of or in addition to velocity estimators. In some examples, the velocity and power estimates may undergo further threshold detection to further reduce noise, as well as segmentation and post-processing such as filling and smoothing. The velocity and power estimates may then be mapped to a desired range of display colors in accordance with a color map. The color data, also referred to as Doppler image data, may then be coupled to the scan converter 330, where the Doppler image data may be converted to the desired image format and overlaid on the B-mode image of the tissue structure to form a color Doppler or a power Doppler image.

Output (e.g., B-mode images, Doppler images) from the scan converter 230, the multiplanar reformatter 232, and/or the volume renderer 234 may be coupled to an image processor 236 for further enhancement, buffering and temporary storage before being displayed on an image display 238. A graphics processor 240 may generate graphic overlays for display with the images. These graphic overlays may contain, e.g., standard identifying information such as patient name, date and time of the image, imaging parameters, and the like. For these purposes the graphics processor may be configured to receive input from the user interface 224, such as a typed patient name or other annotations. The user interface 224 may also be coupled to the multiplanar reformatter 232 for selection and control of a display of multiple multiplanar reformatted (MPR) images.

The system 200 may include local memory 242. Local memory 242 may be implemented as any suitable non-transitory computer readable medium (e.g., flash drive, disk drive). Local memory 242 may store data generated by the system 200 including B-mode images, executable instructions, inputs provided by a user via the user interface 224, or any other information necessary for the operation of the system 200.

As mentioned previously system 200 includes user interface 224. User interface 224 may include display 238 and control panel 252. The display 238 may include a display device implemented using a variety of known display technologies, such as LCD, LED, OLED, or plasma display technology. In some embodiments, display 238 may comprise multiple displays and/or a touch sensitive display. The control panel 252 may be configured to receive user inputs. Example of user inputs may include a number of transmit/receive events, an observation angle for each transmit/receive event, a number of sub-images to acquire from each transmit/receive event, and/or a receive angle for each sub-image. The control panel 252 may include one or more hard controls (e.g., buttons, knobs, dials, encoders, mouse, trackball or others). In some embodiments, the control panel 252 may additionally or alternatively include soft controls (e.g., GUI control elements or simply, GUI controls) provided on a touch sensitive display. In some embodiments, display 238 may be a touch sensitive display that includes one or more soft controls of the control panel 252.

In some embodiments, various components shown in FIG. 2 may be combined. For instance, image processor 236 and graphics processor 240 may be implemented as a single processor. In another example, the B-mode processor 228 and compounding processor 244 may be implemented as a single processor. In some embodiments, various components shown in FIG. 2 may be implemented as separate components. For example, signal processor 226 may be implemented as separate signal processors for each imaging mode (e.g., B-mode, Doppler). In some embodiments, one or more of the various processors shown in FIG. 2 may be implemented by general purpose processors and/or microprocessors configured to perform the specified tasks. In some embodiments, one or more of the various processors may be implemented as application specific circuits. In some embodiments, one or more of the various processors (e.g., image processor 236) may be implemented with one or more graphical processing units (GPU).

Figure 3:
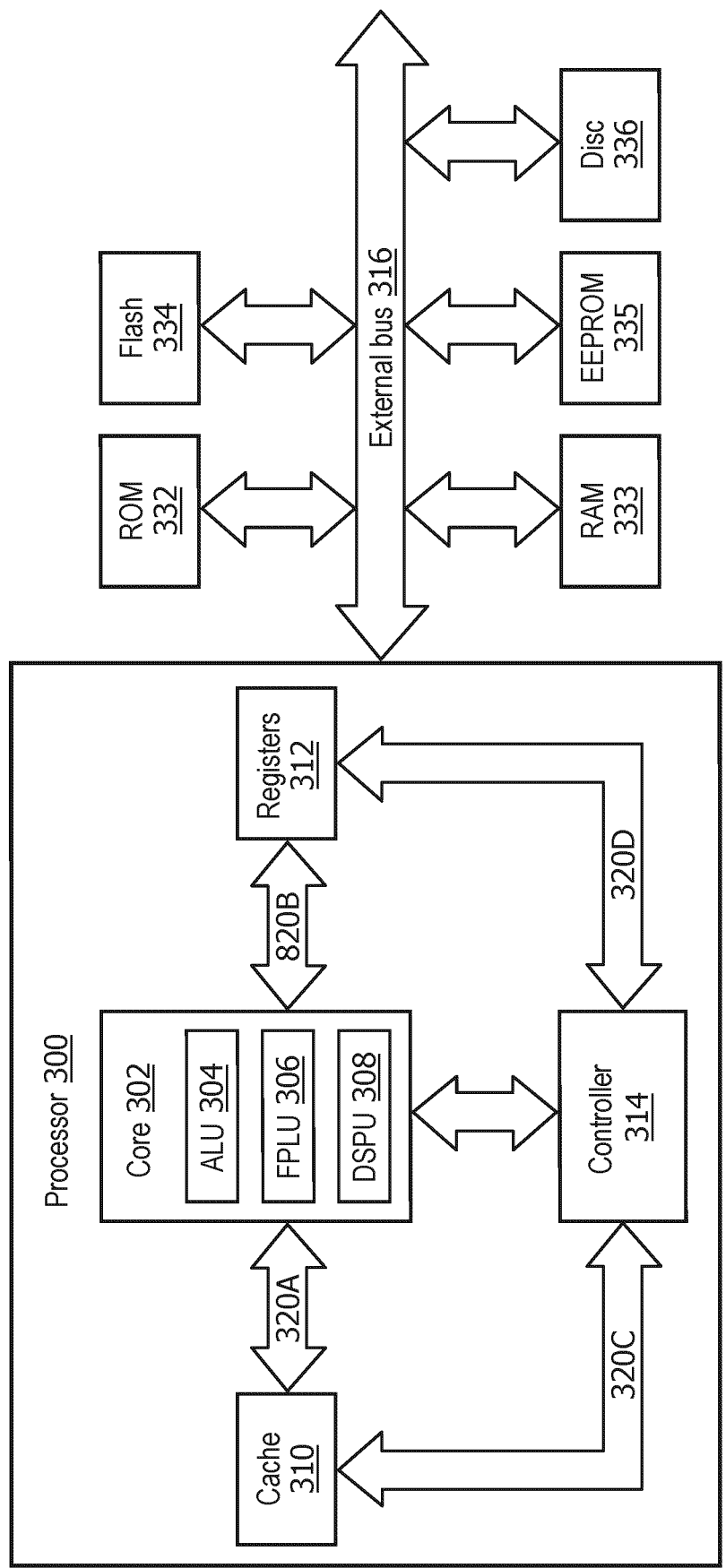
FIG. 3 is a block diagram illustrating an example processor in accordance with some embodiments of the present disclosure.

FIG. 3 is a block diagram illustrating an example processor 300 according to principles of the present disclosure. Processor 300 may be used to implement one or more processors described herein, for example, image processor 236 shown in FIG. 2 or any controller described herein. Processor 300 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 300 may include one or more cores 302. The core 302 may include one or more arithmetic logic units (ALU) 304. In some embodiments, the core 302 may include a floating point logic unit (FPLU) 306 and/or a digital signal processing unit (DSPU) 308 in addition to or instead of the ALU 304.

The processor 300 may include one or more registers 312 communicatively coupled to the core 302. The registers 312 may be implemented using dedicated logic gate circuits (e.g., flip-flops) and/or any memory technology. In some embodiments the registers 312 may be implemented using static memory. The register may provide data, instructions and addresses to the core 302.

In some embodiments, processor 300 may include one or more levels of cache memory 310 communicatively coupled to the core 302. The cache memory 310 may provide computer-readable instructions to the core 302 for execution. The cache memory 310 may provide data for processing by the core 302. In some embodiments, the computer-readable instructions may have been provided to the cache memory 310 by a local memory, for example, local memory attached to the external bus 316. The cache memory 310 may be implemented with any suitable cache memory type, for example, metal-oxide semiconductor (MOS) memory such as static random access memory (SRAM), dynamic random access memory (DRAM), and/or any other suitable memory technology.

The processor 300 may include a controller 314, which may control input to the processor 300 from other processors and/or components included in a system (e.g., control panel 252 and scan converter 230 shown in FIG. 2) and/or outputs from the processor 300 to other processors and/or components included in the system (e.g., display 238 and volume renderer 234 shown in FIG. 2). Controller 314 may control the data paths in the ALU 304, FPLU 306 and/or DSPU 308. Controller 314 may be implemented as one or more state machines, data paths and/or dedicated control logic. The gates of controller 314 may be implemented as standalone gates, FPGA, ASIC or any other suitable technology.

The registers 312 and the cache memory 310 may communicate with controller 314 and core 802 via internal connections 320A, 320B, 320C and 320D. Internal connections may implemented as a bus, multiplexor, crossbar switch, and/or any other suitable connection technology.

Inputs and outputs for the processor 300 may be provided via a bus 316, which may include one or more conductive lines. The bus 316 may be communicatively coupled to one or more components of processor 300, for example the controller 314, cache memory 310, and/or registers 312. The bus 316 may be coupled to one or more components of the system, such as display 238 and control panel 252 mentioned previously.

The bus 316 may be coupled to one or more external memories. The external memories may include Read Only Memory (ROM) 332. ROM 332 may be a masked ROM, Electronically Programmable Read Only Memory (EPROM) or any other suitable technology. The external memory may include Random Access Memory (RAM) 333. RAM 333 may be a static RAM, battery backed up static RAM, Dynamic RAM (DRAM) or any other suitable technology. The external memory may include Electrically Erasable Programmable Read Only Memory (EEPROM) 335. The external memory may include Flash memory 334. The external memory may include a magnetic storage device such as disc 336. In some embodiments, the external memories may be included in a system, such as ultrasound imaging system 200 shown in FIG. 2, for example local memory 242.

Figure 4:
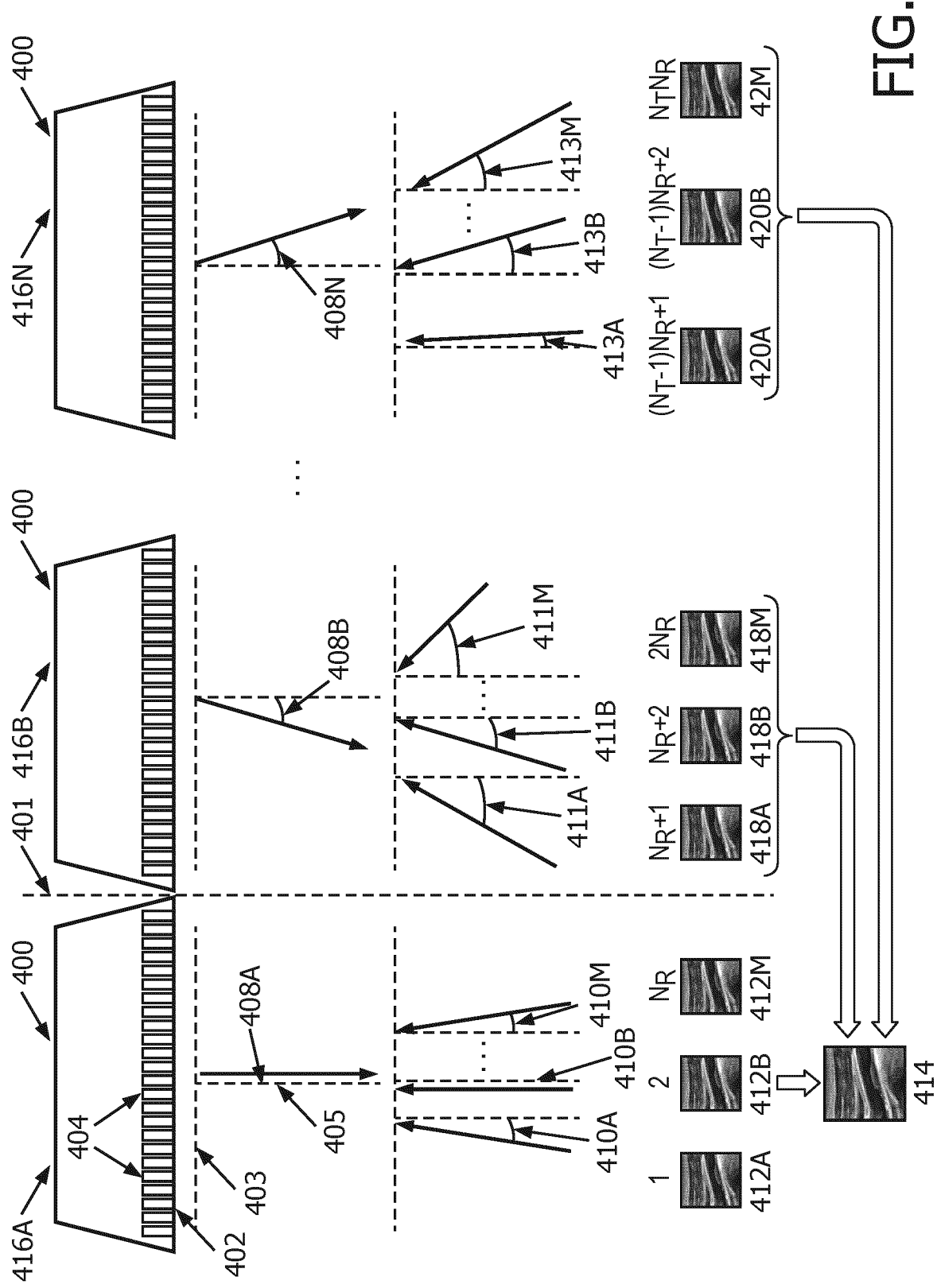
FIG. 4 is an illustration of an example of spatial compounding in accordance with some embodiments of the present disclosure.

FIG. 4 is an illustration of an example of spatial compounding in accordance with examples of the present disclosure. An ultrasound probe 400 may include a transducer array 402 that includes a plurality of transducer elements 404. In some examples, ultrasound probe 400 may be implemented by transducer probe 212 in FIG. 2. The transducer elements 404 may transmit ultrasound beams steered along an observation angle 408 and receive corresponding echoes along receive angles 410A-N. Similar to FIG. 1, the observation angles 408A-N and receive angles 410A-M are shown relative to a plane 405. Plane 405 is normal to a plane 403. Plane 403 is parallel to the face of the transducer array 402. The number of observation angles may be referred to as $N_T$ and the number of receive angles may be referred to as $N_R$. The same ultrasound probe 400 may be used iteratively up to $N_T$ times. Each iteration may use a different transmit angle 408A-N. For each transmit/receive event 416A-N, ultrasound signals are transmitted at a single observation angle 408A-N. For each observation angle 408A-N, multiple sub-images 412A-M, 418A-M, and 420A-M corresponding to receive angles 410A-M, 411A-M, and 413A-M, respectively, are acquired at the same time, leading to a total of $N_T N_R$ sub-images from only $N_T$ angles on transmit.

As mentioned with reference to FIG. 2, the sub-images 412A-M, 418A-M, and/or 420A-M may not be generated for display and the signals associated with the sub-images 412A-M, 418A-M, and/or 420A-M may be compounded to form a final image 414. The number of receive angles 410M, 411M, and/or 413M (e.g., value of $N_R$) has no impact on frame rate when the ultrasound system has enough multilines. As may be understood from FIG. 4, generating beamformed signals corresponding to $N_R$ receive angles may use a total number of multilines equal to $N_R$ multiplied by the number of multilines required for a single sub-image. In other words, the sub-image for each receive angle has its own set of receive lines.

Line 401 serves as a pictorial partition between transmit/receive event 416A and transmit/receive event 416B. As shown on the left-hand side of the dotted line 401, $N_T=1$. That is, for a single transmit/receive event 416A, $N_R$ sub-images are generated, each for a different receive angle 410A-M, which may be compounded into a single image for speckle reduction without a reduction in frame rate. However, more speckle reduction may be achieved with $N_T=2$ or an even larger $N_T$. As shown in the right-hand side of line 401, multiple transmit/receive events 416A-N at different observation angles 408A-N may be performed and the multiple sub-images from all of the transmit/receive events 416A-N may be compounded into a final image 414. However, $N_T$ should be kept small when a higher frame rate is desired. Both the observation angle and the receive angles may vary between transmit/receive events in some examples.

In examples where multiple sub-images are acquired for multiple transmit/receive events, in some embodiments, the beamformer (such as beamformer 222) may generate beamformed signals associated with the sub-images for each transmit/receive event. The beamformed signals for all of the sub-images for all of the transmit/receive events may be provided to a signal processor (such as signal processor 226) and/or B-mode processor (such as B-mode processor 228) and then to a compounding processor (such as compounding processor 244) for compounding. In some examples, the beamformer, signal processor, B-mode processor and/or compounding processor may include a buffer or other memory to store signals from multiple transmit/receive events.

An example of frame rate improvement without loss in performance is provided herein. Consider standard spatial compounding with $N_T=5$ and steering angles of $\theta_{T,1}=\theta_{R,1}=-20°$, $\theta_{T,2}=\theta_{R,2}=-10°$, $\theta_{T,3}=\theta_{R,3}=0°$, $\theta_{T,4}=\theta_{R,4}=10°$, and $\theta_{T,5}=\theta_{R,5}=20°$. Similar speckle reduction performance could be achieved by using principles of the present disclosure with $N_T=2$, $N_R=3$, and transmit/receive steering angles of $\{\theta_{T,1}=-12°, \theta_{R,11}=-28°, \theta_{R,12}=-12°, \theta_{R,13}=4\}$ and $\{\theta_{T,2}=12°, \theta_{R,21}=-4°, \theta_{R,22}=12°, \theta_{R,23}=28°\}$, resulting in average steering angles of $-20°, -12°, -4°, 4°, 12°$, and $20°$. This example is provided for explanatory purposes only and the principles of the present disclosure are not limited to the examples provided. In some examples, a user may determine the number of transmit/receive events, a number of sub-images to acquire, observation angle, and/or receive angle. In some examples, some or all of these parameters may be pre-set in the system.

The observation angle (i.e. the transmit steering angle or transmit angle) and receive angle may be decoupled. That is, they need not be dependent on one another. To decouple the observation and receive angles, a center of the active aperture of the transducer array may be translated as a depth of an ultrasound signal changes (e.g., the depth from which the echoes are received). The active aperture is a set of transducer elements of the transducer array that are receiving the ultrasound signals and transmitting electrical signals responsive to the ultrasound signals to a beamformer.

The translation of the active aperture may be virtual in some examples. That is, all of the transducer elements may receive ultrasound signals and providing signals to the beamformer. The beamformer may receive signals from all of the transducer elements simultaneously. However, for an individual sub-image, the beamformer may select signals from only certain ones of the transducer elements. These certain ones of the transducer elements may constitute the active aperture for the individual sub-image. The beamformer may delay and sum the signals from the active aperture for the individual sub-image to generate the beamformed signal to generate the sub-image.

The beamformer may select signals from certain ones of the transducer elements received from the channels for all of the desired sub-images (e.g., sub-images from all the desired receive angles) at the same time. That is, the beamformer may simultaneously delay and sum signals from multiple active apertures, each active aperture corresponding to a sub-image. The active apertures may overlap in some cases. Thus, in some cases, all of the transducer elements of the transducer array may be active during receive, but the effective aperture for each sub-image may be some subset of the transducer elements of the array defined by the beamformer.

Figure 5:
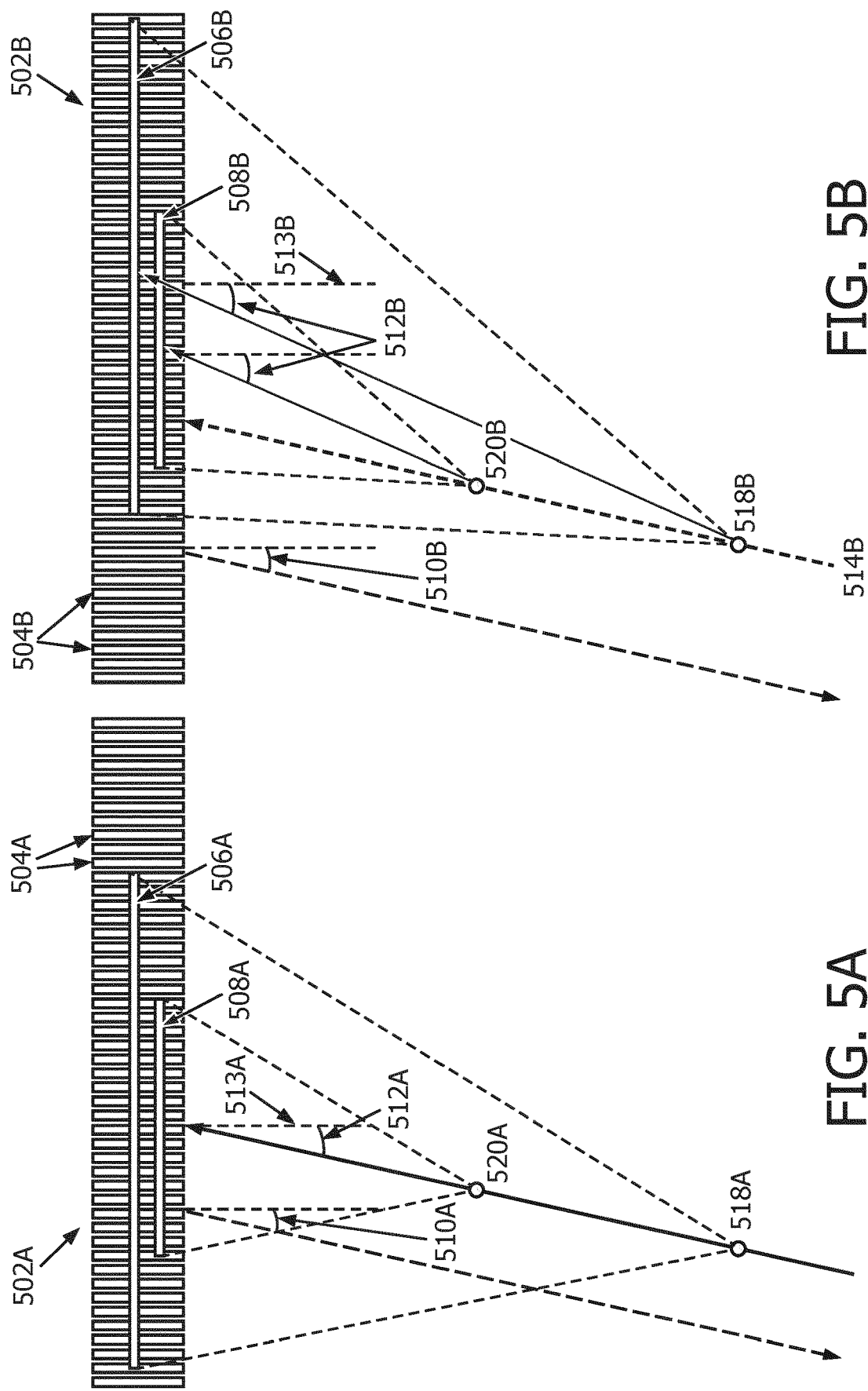
FIGS. 5A and 5B are illustrations of translating an active aperture of a transducer array with depth in accordance with some embodiments of the present disclosure.

FIG. 5A and FIG. 5B are illustrations of translating an active aperture of a transducer array with depth in accordance with examples described herein.

FIG. 5A shows a transducer array 502A that includes multiple transducer elements 504A. The transducer elements 504A that are active for the depth 518A are covered by bar 506A. Transducer elements 504A that are active for the depth 520A are covered by bar 508A. The bars 506A and 508A may be referred to as the active apertures for depths 518A and 520A, respectively. As shown in FIG. 5A, the observation angle 510A and receive angle 512A are equal. The observation angle 510A and receive angle 512A are shown relative to a plane 513A. Plane 513 is orthogonal to a plane (not shown) parallel to the face of the transducer array 502.

FIG. 5B shows a transducer array 502B that includes multiple transducer elements 504B. The transducer elements 504B that are active for the depth 518B are covered by bar 506B. Transducer elements 504B that are active for the depth 520B are covered by bar 508B. The bars 506B and 508B may be referred to as the active apertures for depths 518B and 520B, respectively. As shown in FIG. 5B, the observation angle 510B and receive angle 512B are different. The observation angle 510B and receive angle 512B are shown relative to a plane 513B. Plane 513B is orthogonal to a plane (not shown) parallel to the face of the transducer array 502B. Receive angle 512B is shown twice, once for the depth 518B and once for the depth 520B.

In contrast to active apertures 506A and 508A shown in FIG. 5A, the active apertures 506B and 508B translate i.e. move laterally, across the transducer elements 504B of the transducer array 502B as a function of depth to keep the receive angle 512B constant. However, in other embodiments, different receive angles may be used for different depths (e.g., the receive angle for depth 520B and 518B may be different, as it may also be for receive angles in FIG. 5A). For focused transmits, the observation angle 510B is determined by two points: the center of the transmit aperture (not shown) and the transmit focus (not shown). The pixels that may be imaged for a given transmit/receive event are along a line 514B connecting the center of the transmit aperture and the transmit focus. However, for focusing during receive, receive beamforming is carried out by processing such that pixels to be imaged may be selected arbitrarily. The receive angle 512B may be determined by the center of the receive aperture and the desired pixel of interest. Thus, aperture shifting, as shown by active apertures 506B and 508B, only occurs on receive during a transmit/receive event. However, the active aperture must include transducer elements 504B of the transducer array 502B. Beyond a certain depth (e.g., below depth 518B), the center of the active aperture may no longer be effectively translated. Thus, the receive angle 512B may not be kept constant as a function of depth below the certain depth.

As shown in FIGS. 5A and 5B, the active apertures 506A and 506B include a greater number of transducer elements 504A, 504B than active apertures 508A and 508B. This is because the width of the active aperture decreases with decreasing depth and increases with increasing depth. Thus, the effective receive angle may deviate from the desired angle beyond a depth where the active aperture has reached one or more edges of the array. As may be seen in FIGS. 5A and 5B, some transducer elements 504A, 504B in the active aperture have large looking angles for a given pixel, especially at large beam steering angles. To maximize speckle reduction and lateral resolution preservation, weaker element directivity and/or smaller transducer element width may be desired.

Figure 6:
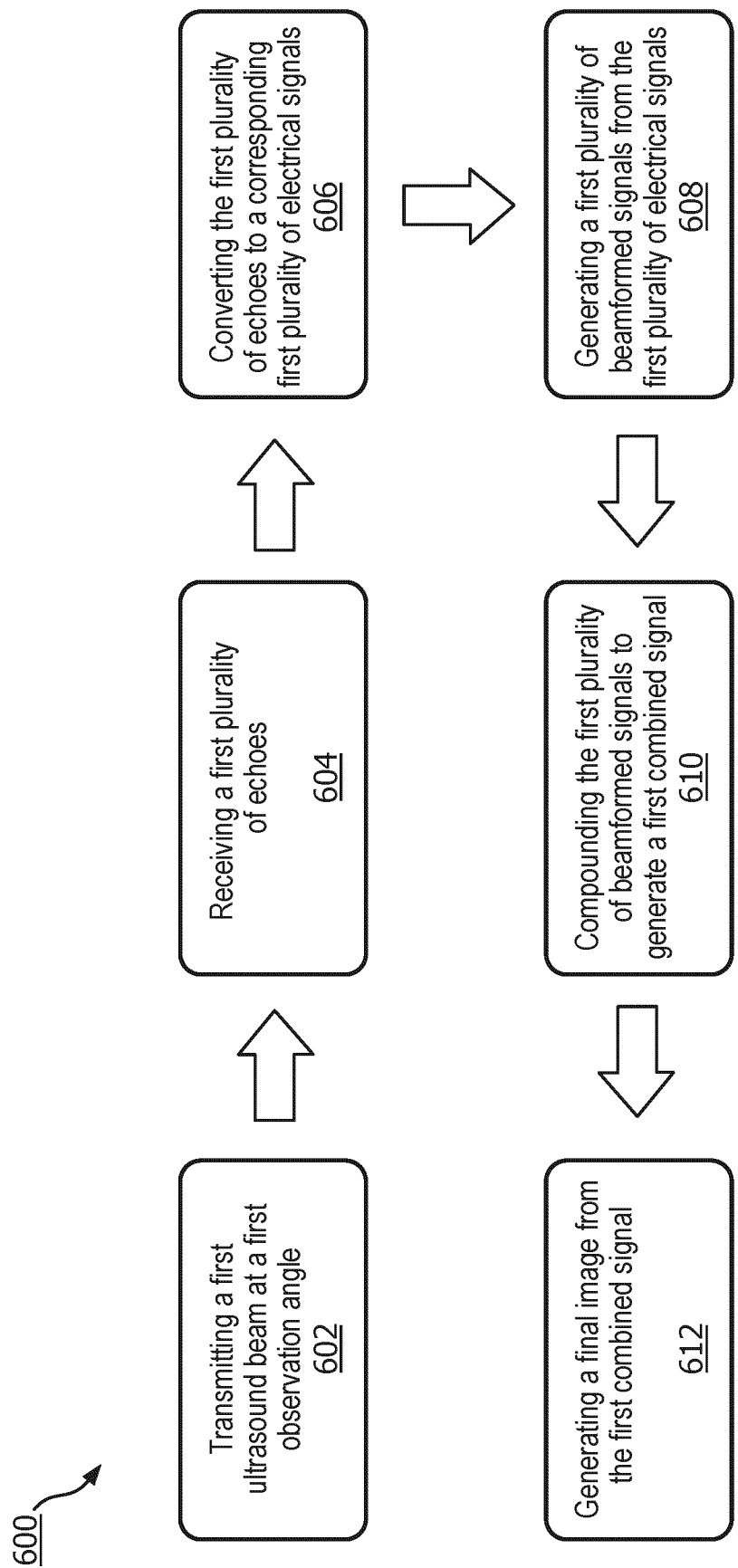
FIG. 6 is a flow chart of a method in accordance with some embodiments of the present disclosure.

FIG. 6 is a flow chart 600 of a method in accordance with examples described herein. At block 602, a step of "transmitting a first ultrasound beam at a first observation angle" may be performed. The transmitting may be performed during a first transmit/receive event. In some examples, the transmitting may be performed by a transducer array of an ultrasound probe, such as transducer array 214 of ultrasound probe 212 shown in FIG. 2. The observation angle may be selected by a user in some examples. At block 604, a step of "receiving a first plurality of echoes" may be performed. The first plurality of echoes may have been generated responsive to the first transmit/receive event. In some examples, the receiving may be performed by the transducer array. At block 606, a step of "converting the first plurality of echoes to a corresponding first plurality of electrical signals" may be performed. In some examples, the converting may be performed by transducer elements of the transducer array, such as transducer array 214 shown in FIG. 2. At block 608, a step of "generating a first plurality of beamformed signals from the first plurality of electrical signals" may be performed. In some examples, the generating may be performed by a beamformer, such as beamformer 222 shown in FIG. 2. In some examples, individual ones of the first plurality of beamformed signals may be associated with corresponding ones of a first plurality of receive angles.

At block 610, a step of "compounding the first plurality of beamformed signals to generate a first combined signal" may be performed. In some examples, the compounding may be performed by a compounding processor, such as compounding processor 244 in FIG. 2. In some examples, the compounding may be performed on signals processed by a signal processor and/or B-mode processor, such as signal processor 226 and B-mode processor 228 shown in FIG. 2. At block 612, a step of "generating a final image from the first combined signal" may be performed. In some examples, the generating of the final image may be performed by compounding processor, scan converter, and/or image processor. For example, scan converter 230 and image processor 236 shown in FIG. 2. In some examples, blocks 602-610 may be repeated for different transmit/receive events for different observation angles and/or different receive angles.

In various embodiments where components, systems and/or methods are implemented using a programmable device, such as a computer-based system or programmable logic, it should be appreciated that the above-described systems and methods may be implemented using any of various known or later developed programming languages, such as "C", "C++", "FORTRAN", "Pascal", and the like. Accordingly, various storage media, such as magnetic computer disks, optical disks, electronic memories and the like, may be prepared that may contain information that may direct a device, such as a computer, to implement the above-described systems and/or methods. Once an appropriate device has access to the information and programs contained on the storage media, the storage media may provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein may be implemented in hardware, software, and/or firmware. Further, the various methods and parameters are included by way of example only and not in any limiting sense. In view of this disclosure, those of ordinary skill in the art may implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein and shown in FIG. 3.

Although the present system may have been described with particular reference to an ultrasound imaging system, it is also envisioned that the present system may be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems may be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present systems and methods and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. A medical imaging system comprising:
   a transducer array, wherein the transducer array is configured to transmit an ultrasound beam, receive echoes responsive to the ultrasound beam, and generate electrical signals corresponding to the echoes;
   a controller circuit, wherein the controller circuit is configured to cause the transducer array to transmit the ultrasound beam at an observation angle for a transmit/receive event; and
   a beamformer configured to receive the electrical signals from a first plurality of receive angles from the transmit/receive event,
   wherein the beamformer is a multiline beamformer configured to receive a plurality of sets of multiple receive lines wherein each set of the plurality of sets of multiple receive lines corresponds to a different single receive angle of the first plurality of receive angles and the beamformer is further configured to generate a first plurality of beamformed signals,
   wherein each of the first plurality of beamformed signals is associated with a corresponding one of the first plurality of receive angles,
   wherein the medical imaging system is configured to compound the first plurality of beamformed signals to generate a final image.

2. The medical imaging system of claim 1, further comprising a compounding processor, wherein the compounding processor is configured to compound the first plurality of beamformed signals to generate the final image.

3. The medical imaging system of claim 1, further comprising a signal processor, wherein the signal processor is configured to receive the first plurality of beamformed signals and perform noise reduction on the first plurality of beamformed signals.

4. The medical imaging system of claim 1, further comprising a B-mode processor, wherein the B-mode processor is configured to receive the first plurality of beamformed signals and perform amplitude detection on the first plurality of beamformed signals.

5. The medical imaging system of claim 1,
   wherein the controller circuit is configured to cause the transducer array to transmit the ultrasound beam at a second observation angle for a second transmit/receive event; and
   wherein the beamformer is configured to receive the electrical signals from the second transmit/receive event and to generate a second plurality of beamformed signals, each of the second plurality of beamformed signals associated with corresponding one of a second plurality of receive angles,
   wherein the medical imaging system is further configured to combine the first plurality of beamformed signals and the second plurality of beamformed signals into a combined signal.

6. The medical imaging system of claim 5, wherein the first plurality of receive angles are different than the second plurality of receive angles.

7. The medical imaging system of claim 5, wherein the second observation angle is different than the first observation angle.

8. The medical imaging system of claim 5, wherein the beamformer includes a buffer for storing the first plurality of beamformed signals.

9. The medical imaging system of claim 1, further comprising a user interface comprising a first control for receiving a user input indicative of a value of the observation angle.

10. The medical imaging system of claim 9, wherein the user interface comprises a second control for receiving a user input indicative of a value for at least one of the first plurality of receive angles.

11. The medical imaging system of claim 9, wherein the user interface comprises another control for receiving a user input indicative of a number of the first plurality of receive angles.

12. The medical imaging system of claim 1, wherein the beamformer is configured to set a first active aperture associated with a first one of the first plurality of receive angles and a second active aperture associated with a second one of the first plurality of receive angles, wherein the first active aperture overlaps with the second active aperture.

13. The medical imaging system of claim 1, wherein a position of an active aperture of the transducer array varies with a value of a receive angle of the first plurality of receive angles.

14. The medical imaging system of claim 13, wherein a width of the active aperture of the transducer array varies with a depth of the echoes.

15. A method, comprising:
transmitting a first ultrasound beam at a first observation angle during a first transmit/receive event;
receiving a first plurality of echoes generated responsive to the first transmit/receive event;
converting the first plurality of echoes to a corresponding first plurality of electrical signals;
generating a first plurality of beamformed signals from the first plurality of electrical signals with a multiline beamformer, wherein the multiline beamformer is configured to receive a plurality of sets of multiple receive lines wherein each set of multiple receive lines corresponds to a different single receive angle of a first plurality of receive angles and wherein individual ones of the first plurality of beamformed signals are associated with corresponding ones of the first plurality of receive angles;
compounding the first plurality of beamformed signals to generate a first combined signal; and
generating a final image from the first combined signal.

16. The method of claim 15, further comprising:
transmitting a second ultrasound beam at a second observation angle during a second transmit/receive event;
receiving a second plurality of echoes generated responsive to the second transmit/receive event;
converting the second plurality of echoes to a corresponding second plurality of electrical signals;
generating a second plurality of beamformed signals from the second plurality of electrical signals, wherein individual ones of the second plurality of beamformed signals are associated with corresponding ones of a second plurality of receive angles;
compounding the second plurality of beamformed signals and the first plurality of beamformed signals to generate a second combined signal; and
generating the final image from the second combined signal.

17. The method of claim 16, wherein receive angles of the first plurality of receive angles are different from receive angles of the second plurality of receive angles.

18. The method of claim 15, wherein compounding the first plurality of beamformed signals comprises summing the first plurality of beamformed signals and taking an average.

19. The method of claim 15, wherein compounding is performed by a compounding processor.

20. The medical imaging system of claim 12, wherein the first and second active apertures are set virtually by the beamformer, wherein the beamformer receives signals from all transducer elements of the transducer array and the beamformer selects signals from certain ones of the transducer elements to virtually set the first and second active apertures.

21. The medical imaging system of claim 1, further configured to compound the first plurality of beamformed signals by summing the first plurality of beamformed signals and taking an average.

22. The medical imaging system of claim 1, further configured to compound the first plurality of beamformed signals by summing the first plurality of beamformed signals.

23. The medical imaging system of claim 1, further configured to compound the first plurality of beamformed signals by taking a maximum value for each one of the first plurality of beamformed signals.

* * * * *